United States Patent
Halbritter et al.

(10) Patent No.: US 10,485,465 B2
(45) Date of Patent: Nov. 26, 2019

(54) PULSE OXIMETRY DEVICE AND METHOD OF OPERATING A PULSE OXIMETRY DEVICE

(71) Applicant: OSRAM Opto Semiconductors GmbH, Regensburg (DE)

(72) Inventors: Hubert Halbritter, Dietfurt-Toeging (DE); Michael Klein, Regensburg (DE); David O'Brien, Bad Abbach (DE)

(73) Assignee: OSRAM Opto Semiconductors GmbH, Regensburg (DE)

( * ) Notice: Subject to any disclaimer, the term of this patent is extended or adjusted under 35 U.S.C. 154(b) by 159 days.

(21) Appl. No.: 15/526,495

(22) PCT Filed: Dec. 3, 2015

(86) PCT No.: PCT/EP2015/078573
§ 371 (c)(1),
(2) Date: May 12, 2017

(87) PCT Pub. No.: WO2016/087609
PCT Pub. Date: Jun. 9, 2016

(65) Prior Publication Data
US 2017/0325729 A1 Nov. 16, 2017

(30) Foreign Application Priority Data
Dec. 4, 2014 (DE) .......... 10 2014 117 879

(51) Int. Cl.
*A61B 5/1455* (2006.01)
*A61B 5/00* (2006.01)

(52) U.S. Cl.
CPC ........ *A61B 5/14552* (2013.01); *A61B 5/7214* (2013.01); *A61B 2562/0238* (2013.01)

(58) Field of Classification Search
CPC .............. A61B 5/14552; A61B 5/7214; A61B 2562/0238
See application file for complete search history.

(56) References Cited

U.S. PATENT DOCUMENTS

| 4,907,594 A | 3/1990 | Muz |
| 5,421,329 A | 6/1995 | Casciani et al. |

(Continued)

FOREIGN PATENT DOCUMENTS

| CN | 1141585 A | 1/1997 |
| CN | 1915167 A | 2/2007 |

(Continued)

OTHER PUBLICATIONS

Notice of Reasons for Rejection dated May 29, 2018, of corresponding Japanese Application No. 2017-526100 in English.

(Continued)

*Primary Examiner* — Matthew Kremer
*Assistant Examiner* — Samuel C Kim
(74) *Attorney, Agent, or Firm* — DLA Piper LLP (US)

(57) ABSTRACT

A pulse oximetry device includes a light emission device configured to emit light with a wavelength in a first wavelength interval and light with a wavelength in a second wavelength interval, a first light detector configured to detect light with a wavelength in the first wavelength interval, but not to respond to light with a wavelength in the second wavelength interval, and a second light detector configured to detect light with a wavelength in the first wavelength interval and detect light with a wavelength in the second wavelength interval, wherein the first light detector has a first light reception surface, the second light detector has a second light reception surface, and the first light (Continued)

reception surface and the second light reception surface are arranged in a common plane and are interleaved with one another.

17 Claims, 4 Drawing Sheets

(56) References Cited

U.S. PATENT DOCUMENTS

| | | | |
|---|---|---|---|
| 5,842,981 | A | 12/1998 | Larsen et al. |
| 6,181,959 | B1 | 1/2001 | Schöllermann et al. |
| 6,549,795 | B1 | 4/2003 | Chance |
| 2002/0042558 | A1 | 4/2002 | Mendelson |
| 2006/0129204 | A1* | 6/2006 | Pless ............... A61B 5/14553 607/45 |
| 2007/0129613 | A1 | 6/2007 | Rochester et al. |
| 2009/0112071 | A1* | 4/2009 | LeBoeuf ............ A61B 5/02116 600/301 |
| 2009/0177053 | A1 | 7/2009 | Merchant et al. |
| 2009/0240125 | A1 | 9/2009 | Such et al. |
| 2010/0056887 | A1 | 3/2010 | Kimura et al. |
| 2010/0210930 | A1* | 8/2010 | Saylor ............... A61B 5/14532 600/323 |
| 2013/0225952 | A1 | 8/2013 | Lin et al. |

FOREIGN PATENT DOCUMENTS

| | | |
|---|---|---|
| CN | 101080192 A | 11/2007 |
| DE | 37 23 881 A1 | 1/1989 |
| DE | 697 24 822 T2 | 7/2004 |
| DE | 695 33 927 T2 | 6/2005 |
| JP | 2007-518467 | 7/2007 |
| WO | 94/23643 A1 | 10/1994 |
| WO | 95/02358 A1 | 1/1995 |
| WO | 97/36538 A1 | 10/1997 |
| WO | 2007/008057 A1 | 1/2007 |

OTHER PUBLICATIONS

First Office Action dated Jun. 28, 2019, of counterpart Chinese Application No. 201580066060.8, along with an English translation.

* cited by examiner

PULSE OXIMETRY DEVICE AND METHOD OF OPERATING A PULSE OXIMETRY DEVICE

TECHNICAL FIELD

This disclosure relates to a pulse oximetry device and a method of operating a pulse oximetry device.

BACKGROUND

Pulse oximetry devices for non-invasive determination of an arterial oxygen saturation in the blood of a human patient are known. In such pulse oximetry devices, determination of the arterial oxygen saturation is carried out by a light absorption measurement while shining light through the skin of the patient.

SUMMARY

We provide a pulse oximetry device including a light emission device configured to emit light with a wavelength in a first wavelength interval and light with a wavelength in a second wavelength interval, a first light detector configured to detect light with a wavelength in the first wavelength interval, but not to respond to light with a wavelength in the second wavelength interval, and a second light detector configured to detect light with a wavelength in the first wavelength interval and detect light with a wavelength in the second wavelength interval, wherein the first light detector has a first light reception surface, the second light detector has a second light reception surface, and the first light reception surface and the second light reception surface are arranged in a common plane and are interleaved with one another.

We also provide a method of operating a pulse oximetry device including emitting light with a wavelength in a first wavelength interval and simultaneously emitting light with a wavelength in a second wavelength interval; recording a first measurement signal with a first light detector configured to detect light with a wavelength in the first wavelength interval, but not to respond to light with a wavelength in the second wavelength interval; recording a second measurement signal with a second light detector configured to detect light with a wavelength in the first wavelength interval and detect light with a wavelength in the second wavelength interval, wherein the first light detector has a first light reception surface, the second light detector has a second light reception surface, and the first light reception surface and the second light reception surface are arranged in a common plane and are interleaved with one another; and calculating an oxygen saturation from the first measurement signal and the second measurement signal.

Figure 1:
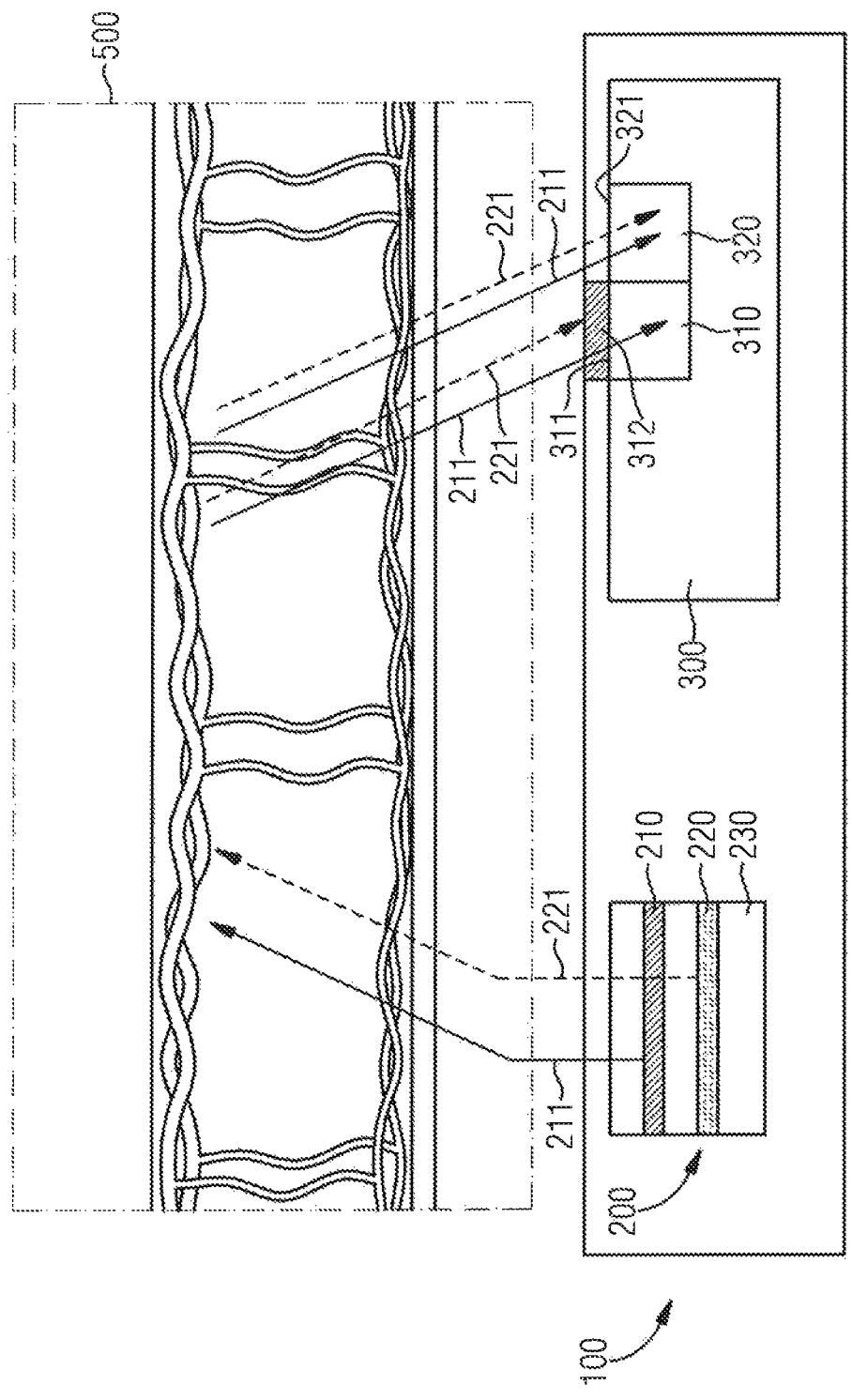
FIG. 1 schematically shows a pulse oximetry device having a light emission device and a light detection device.

LIST OF REFERENCES 100 pulse oximetry device
200 light emission device
210 first light-emitting diode structure
211 light with a wavelength in a first wavelength interval
220 second light-emitting diode structure
221 light with a wavelength in a second wavelength interval
230 light-emitting diode chip
231 first light-emitting diode chip
232 second light-emitting diode chip
300 light detection device
310 first light detector
311 first light reception surface
312 filter
320 second light detector
321 second light reception surface
400 housing
401 upper side
410 emitter cavity
411 wall
420 further emitter cavity
430 detector cavity
440 diaphragm structure
450 cover structure
500 body part

DETAILED DESCRIPTION

Our pulse oximetry device comprises a light emission device configured to emit light with a wavelength in a first wavelength interval and light with a wavelength in a second wavelength interval, a first light detector configured to detect light with a wavelength in the first wavelength interval, but not to respond to light with a wavelength in the second wavelength interval, and a second light detector configured to detect light with a wavelength in the first wavelength interval and detect light with a wavelength in the second wavelength interval.

The pulse oximetry device has only a small number of components and can, therefore, be configured compactly and produced economically. Since the pulse oximetry device has two light detectors, which make it possible to discriminate between light with a wavelength in the first wavelength interval and light with a wavelength in the second wavelength interval, the light emission device of this pulse oximetry device can simultaneously emit light with a wavelength in the first wavelength interval and light with a wavelength in the second wavelength interval. Operation of the pulse oximetry device is therefore advantageously particularly straightforwardly possible.

The first wavelength interval and the second wavelength interval need not overlap one another. Advantageously, the light with a wavelength in the wavelength interval and the light with a wavelength in the second interval may thereby differ significantly so that clear discrimination between oxygenated hemoglobin and deoxygenated hemoglobin is made possible.

The first wavelength interval or the second wavelength interval may lie below 810 nm, and may in particular comprise a wavelength of 660 nm. The other wavelength interval in this case lies above 810 nm, and may in particular comprise a wavelength of 940 nm. Light with wavelengths in these wavelength intervals has proven particularly suitable for use in pulse oximetry devices.

The first light detector may have a filter configured to filter out light with a wavelength in the second wavelength interval. It is thereby possible to ensure that the first light detector does not respond to light with a wavelength in the second wavelength interval. In this way, comparison of measurement signals delivered by the first light detector and the second light detector makes it possible to discriminate between the signal components caused by light with a wavelength in the first wavelength interval and by light with a wavelength in the second wavelength interval.

The first light detector may have a first light reception surface. In this case, the second light detector has a second light reception surface. The first light reception surface and the second light reception surface are arranged in a common plane and interleaved with one another. Advantageously, homogeneous illumination of the first light reception surface of the first light detector and the second light reception surface of the second light detector can thereby be ensured. This advantageously avoids a measurement signal determined by the pulse oximetry device being vitiated, for example, by geometrical shadowing.

The light emission device may be configured to emit light with a wavelength in the second wavelength interval with a higher power than light with a wavelength in the first wavelength interval, in particular with a power at least four times as high, in particular with a power at least eight times as high. For example, the light emission device may be configured to emit light with a wavelength in the second wavelength interval with a power nine times as high as light with a wavelength in the first wavelength interval. The achievable effect is that a measurement signal determined by the second light detector of the pulse oximetry device is dominated by the detection of light with a wavelength in the second wavelength interval, while the detection of light with a wavelength in the first wavelength interval is negligible. In this way, the first light detector and the second light detector of the pulse oximetry device advantageously allow almost separate detection of light with a wavelength in the first wavelength interval and light with a wavelength in the second wavelength interval.

The light emission device may have a first light-emitting diode structure configured to emit light with a wavelength in the first wavelength interval, and a second light-emitting diode structure configured to emit light with a wavelength in the second wavelength interval. Since, in the pulse oximetry device, it is not necessary to emit light with a wavelength in the first wavelength interval and light with a wavelength in the second wavelength interval separately from one another, the first light-emitting diode structure and the second light-emitting diode structure of the light emission device may be interleaved such that the first light-emitting diode structure and the second light-emitting diode structure are always operated together so that the light emission device can advantageously be configured particularly simply.

The first light-emitting diode structure and the second light-emitting diode structure may be arranged in a common light-emitting diode chip. Advantageously, the light emission device is therefore configured particularly compactly.

The first light-emitting diode structure and the second light-emitting diode structure may be arranged/stacked on top of one another. In this case, the first light-emitting diode structure and the second light-emitting diode structure may, for example, be configured as layers of the common light-emitting diode chip arranged on top of one another. The first light-emitting diode structure and the second light-emitting diode structure may in this case electrically connect in series. Advantageously, the light emission device has particularly compact external dimensions and can be obtained economically. By electrical interconnection of the first light-emitting diode structure and the second light-emitting diode structure of the light emission device in series, it is advantageously possible to ensure that electrical currents with the same current strength always flow through the first light-emitting diode structure and the second light-emitting diode structure.

The light emission device may have a first light-emitting diode chip having the first light-emitting diode structure, and a second light-emitting diode chip having the second light-emitting diode structure. Advantageously, the light-emitting diode chips of the light emission device can therefore be formed by economically available standard components.

The pulse oximetry device may have a housing with an emitter cavity and a detector cavity. In this case, the light emission device is arranged in the emitter cavity, while the first light detector is arranged in the detector cavity. Advantageously, the housing of the pulse oximetry device may in this case be configured extremely compactly. By virtue of the arrangement of the light emission device and the first light detector in separate cavities, undesired direct crosstalk between the light emission device and the first light detector, which impairs the measurement quality, is advantageously avoided.

The second light detector may likewise be arranged in the detector cavity. Advantageously, it is thereby possible to ensure that the first light detector and the second light detector are arranged close to one another so that vitiation by geometrical effects of a measurement signal determined by the pulse oximetry device can be avoided.

The emitter cavity and the detector cavity may be open to a common surface of the housing. During operation of the pulse oximetry device, this common surface of the housing of the pulse oximetry device may face toward a human patient's body part to be examined.

A wall of the emitter cavity may form an optical reflector. Advantageously, the optical reflector formed by the wall of the emitter cavity may cause concentration of the light emitted by the light emission device so that a higher radiation intensity of the light emitted by the light emission device can also be obtained. This, for example, may make it possible for the light emitted by the light emission device of the pulse oximetry device to reach deeper skin layers of a patient to be examined so that an increased measurement accuracy can be made possible.

The housing may have a further emitter cavity in which a further light emission device is arranged. This can make it possible to illuminate with the pulse oximetry device a larger skin surface of a patient to be examined, which may lead to an improved signal-to-noise ratio.

A method of operating a pulse oximetry device comprises steps of emitting light with a wavelength in a first wavelength interval, and simultaneously emitting light with a wavelength in a second wavelength interval, recording a first measurement signal with a first light detector configured to detect light with a wavelength in the first wavelength interval, but not to respond to light with a wavelength in the second wavelength interval, recording a second measurement signal with a second light detector configured to detect light with a wavelength in the first wavelength interval and detect light with a wavelength in the second wavelength interval, and calculating an oxygen saturation from the first measurement signal and the second measurement signal.

Since the light with a wavelength in the first wavelength interval and the light with a wavelength in the second wavelength interval are simultaneously emitted in this method, the method can advantageously be carried out particularly simply and rapidly. The method may in this case advantageously be used to operate a pulse oximetry device having only a small number of components, and can therefore be economically obtained.

In this method, the recording of the first measurement signal with the first light detector and of the second measurement signal with the second light detector allows separation of the component of the light with a wavelength in the first wavelength interval and the component of the light with a wavelength in the second wavelength interval. This is achieved by the first measurement signal being recorded with the first light detector which responds only to light with a wavelength in the first wavelength interval, but not to light with a wavelength in the second wavelength interval.

A difference signal may be formed from the difference of the first measurement signal and the second measurement signal. In this case, the oxygen saturation is calculated from the first measurement signal and the difference signal. Advantageously, the formed difference signal essentially indicates the component of the light with a wavelength in the second wavelength interval. Use of the first measurement signal and the difference signal therefore allows particularly accurate calculation of the oxygen saturation.

The light with a wavelength in the second wavelength interval may be emitted with a higher power than the light with a wavelength in the first wavelength interval, in particular with a power that is at least four times as high, in particular with a power that is at least eight times as high. For example, the light with a wavelength in the second wavelength interval may be emitted with a power that is nine times as high as the light with a wavelength in the first wavelength interval. Advantageously, the effect thereby achieved is that the second measurement signal, recorded with the second light detector, is dominated by the component of the light with a wavelength in the second wavelength interval. In this way, discrimination of the components of the light with a wavelength in the first wavelength interval and the light with a wavelength in the second wavelength interval is facilitated so that the method advantageously allows particularly accurate calculation of the oxygen saturation.

The above-described properties, features and advantages, as well as the way in which they are achieved, will become more clearly and readily comprehensible in conjunction with the following description of the examples, which will be explained in more detail in connection with the drawings.

FIG. 1 shows a highly schematized representation of a pulse oximetry device 100. The pulse oximetry device 100 may be used for non-invasive determination of an oxygen saturation in the blood of a patient. Determination of the oxygen saturation is carried out by a light absorption measurement while illuminating the skin of a body part 500, for example, a finger of the patient.

The pulse oximetry device 100 comprises a light emission device 200 and a light detection device 300.

The light emission device 200 comprises a first light-emitting diode structure 210 and a second light-emitting diode structure 220. The first light-emitting diode structure 210 is configured to emit light 211 with a wavelength in a first wavelength interval. The second light-emitting diode structure 220 is configured to emit light 221 with a wavelength in a second wavelength interval.

The first wavelength interval and the second wavelength interval preferably do not overlap one another. Preferably, one of the wavelength intervals lies below 810 nm, the other wavelength interval lies above 810 nm. The wavelength interval lying below 810 nm preferably comprises a wavelength of 660 nm. The wavelength interval lying above 810 nm preferably comprises a wavelength of 940 nm. In the example shown in FIG. 1, the first wavelength interval lies below 810 nm and comprises the wavelength of 660 nm. The second wavelength interval in this example lies above 810 nm and comprises the wavelength of 940 nm. Preferably, the first light-emitting diode structure 210 is configured in this example to emit light 211 with a wavelength of about 660 nm. The second light-emitting diode structure 220 is in this example preferably configured to emit light 221 with a wavelength of about 940 nm.

In the example of pulse oximetry device 100 as represented in FIG. 1, the first light-emitting diode structure 210 and the second light-emitting diode structure 220 of the light emission device 200 are arranged in a common light-emitting diode chip 230. In this case, the first light-emitting diode structure 210 and the second light-emitting diode structure 220 are arranged/stacked on top of one another in the light-emitting diode chip 230. The light-emitting diode chip 230 may also be referred to as a stack LED or a dual-wavelength LED.

The light detection device 300 of the pulse oximetry device 100 comprises a first light detector 310 and a second light detector 320. The first light detector 310 has a first light reception surface 311. The second light detector 320 has a second light reception surface 321. The first light detector 310 and the second light detector 320 of the light detection device 300 may, for example, be configured as photodiodes.

The first light detector 310 of the light detection device 300 of the pulse oximetry device 100 is configured to detect light 211 with a wavelength in the first wavelength interval striking the first light detector 310, but not to respond to light 221 with a wavelength in the second wavelength interval striking the first light detector 310. The first light detector 310 is configured to deliver a first measurement signal, the size of which depends on the brightness of the light 211 with a wavelength in the first wavelength interval striking the first light detector 310. Light 221 with a wavelength in the second wavelength interval striking the first light detector 310 preferably does not influence the size of the first measurement signal delivered by the first light detector 310, or influences it only to an extent which is as small as possible. This is achieved in the first light detector 310 of the light detection device 300 by a filter 312 arranged on the first light reception surface 311 of the first light detector 310, this filter being configured to filter out light 221 with a wavelength in the second wavelength interval 221, but to transmit light 211 with a wavelength in the first wavelength interval.

The second light detector 320 of the light detection device 300 of the pulse oximetry device 100 is configured to detect light 211 with a wavelength in the first wavelength interval striking the second light reception surface 321 of the second light detector 320 and light 221 with a wavelength in the second wavelength interval striking the second light reception surface 321. The second light detector 320 is configured to generate a second measurement signal, the size of which depends on the brightness of the light 211 with a wavelength in the first wavelength interval striking the second light reception surface 321 and on the brightness of the light 221 with a wavelength in the second wavelength interval striking the second light reception surface 321.

Light 211 with a wavelength in the first wavelength interval and light 221 with a wavelength in the second wavelength interval, shining into the body part 500, is absorbed with different strength depending on the arterial oxygen saturation. From a measurement of the brightness of the light 211 with a wavelength in the first wavelength interval and light 221 with a wavelength in the second wavelength interval, reflected in the body part 500 or transmitted through the body part 500, it is therefore possible to determine the arterial oxygen saturation.

To this end, it is necessary to determine the brightness of the reflected or transmitted light 211 with a wavelength in the first wavelength interval and the brightness of the reflected or transmitted light 221 with a wavelength in the second wavelength interval at least approximately separately. By the light emission device 200 of the pulse oximetry device 100, light 211 with a wavelength in the first wavelength interval and light 221 with a wavelength in the second wavelength interval is simultaneously emitted. It is therefore necessary to record the brightness of the reflected or transmitted light 211 with a wavelength in the first wavelength interval and the brightness of the reflected or transmitted light 221 with a wavelength in the second wavelength interval at least approximately separately with the aid of the light detection device 300.

One possibility consists in configuring the light emission device 200 such that light 221 with a wavelength in the second wavelength interval is emitted with a higher power than light 211 with a wavelength in the first wavelength interval. In this case, the light 221 is preferably emitted with a power that is at least four times as high, in particular with a power that is at least eight times as high, as the light 211 with a wavelength in the first wavelength interval. For example, the light 221 with a wavelength in the second wavelength interval may be emitted with a power that is nine times as high as the light 211 with a wavelength in the first wavelength interval.

In this case, the second measurement signal recorded by the second light detector 320 of the light detection device 300 is dominated by the brightness of the light 221 with a wavelength in the second wavelength interval striking the second light reception surface 321 of the second light detector 320, while the influence of the light 221 with a wavelength in the first wavelength interval striking the second light reception surface 321 of the second light detector 320 is negligibly small. This makes it possible to assume as an approximation that the second measurement signal recorded by the second light detector 320 of the light detection device 300 depends only on the brightness of the reflected or transmitted light 221 with a wavelength in the second wavelength interval.

The first measurement signal recorded by the first light detector 310 of the light detection device 300 indicates the brightness of the reflected or transmitted light 211 with a wavelength in the first wavelength interval. This makes it possible to calculate the arterial oxygen saturation in the body part 500 from the measurement signal delivered by the first light detector 310 and the measurement signal delivered by the second light detector 320, the systematic error entailed being small.

An alternative possibility consists of subtracting the first measurement signal recorded by the first light detector 310 of the light detection device 300 from the second measurement signal recorded by the second light detector 320 of the light detection device 300. The formed difference signal depends approximately only on the brightness of the reflected or transmitted light 221 with a wavelength in the second wavelength interval striking the second light reception surface 321 of the second light detector 320. In this case, it is unimportant whether the light 211 with a wavelength in the first wavelength interval and the light 221 with a wavelength in the second wavelength interval are emitted with the same power or different powers by the light emission device 200 of the pulse oximetry device 100. The first measurement signal recorded by the first light detector 310 of the light detection device 300 depends on the brightness of the reflected or transmitted light 211 with a wavelength in the first wavelength interval striking the first light reception surface 311 of the first light detector 310. This makes it possible to calculate the arterial oxygen saturation in the body part 500 from the first measurement signal delivered by the first light detector 310 and the second measurement signal delivered by the second light detector 320.

Figure 2:
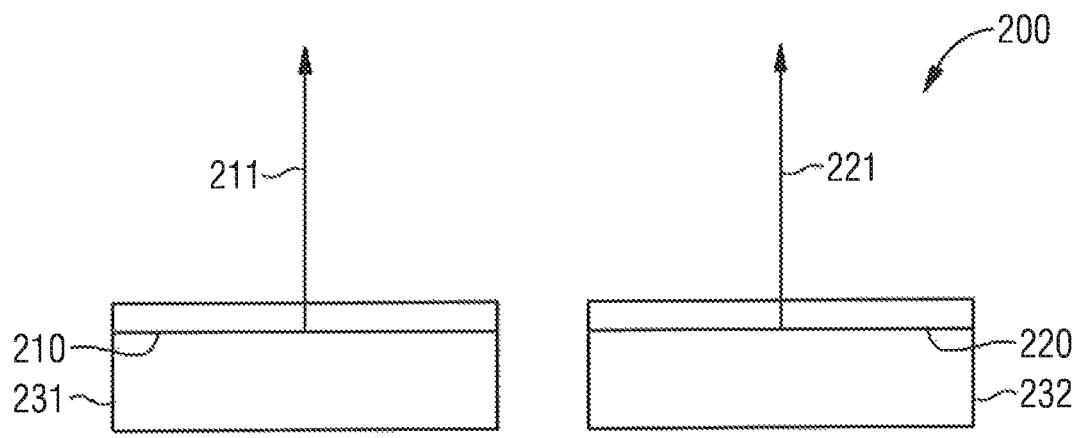
FIG. 2 schematically shows a light emission device according to an alternative example.

FIG. 2 shows a schematic sectional side view of the light emission device 200 of the pulse oximetry device 100 according to an alternative example. In the example represented in FIG. 2, the light emission device 200 also comprises a first light-emitting diode structure 210 that emits light 211 with a wavelength in the first wavelength interval and a second light-emitting diode structure 220 that emits light 221 with a wavelength in the second wavelength interval. In the example of the light emission device 200 as represented in FIG. 2, however, the first light-emitting diode structure 210 and the second light-emitting diode structure 220 are not integrated into a common light-emitting diode chip. Instead, the first light-emitting diode structure 210 is arranged in a first light-emitting diode chip 231 and the second light-emitting diode structure 220 is arranged in a second light-emitting diode chip 232. The first light-emitting diode chip 231 and the second light-emitting diode chip 232 together form the light emission device 200. Preferably, the first light-emitting diode chip 231 and the second light-emitting diode chip 232 are arranged close to one another.

Figure 3:
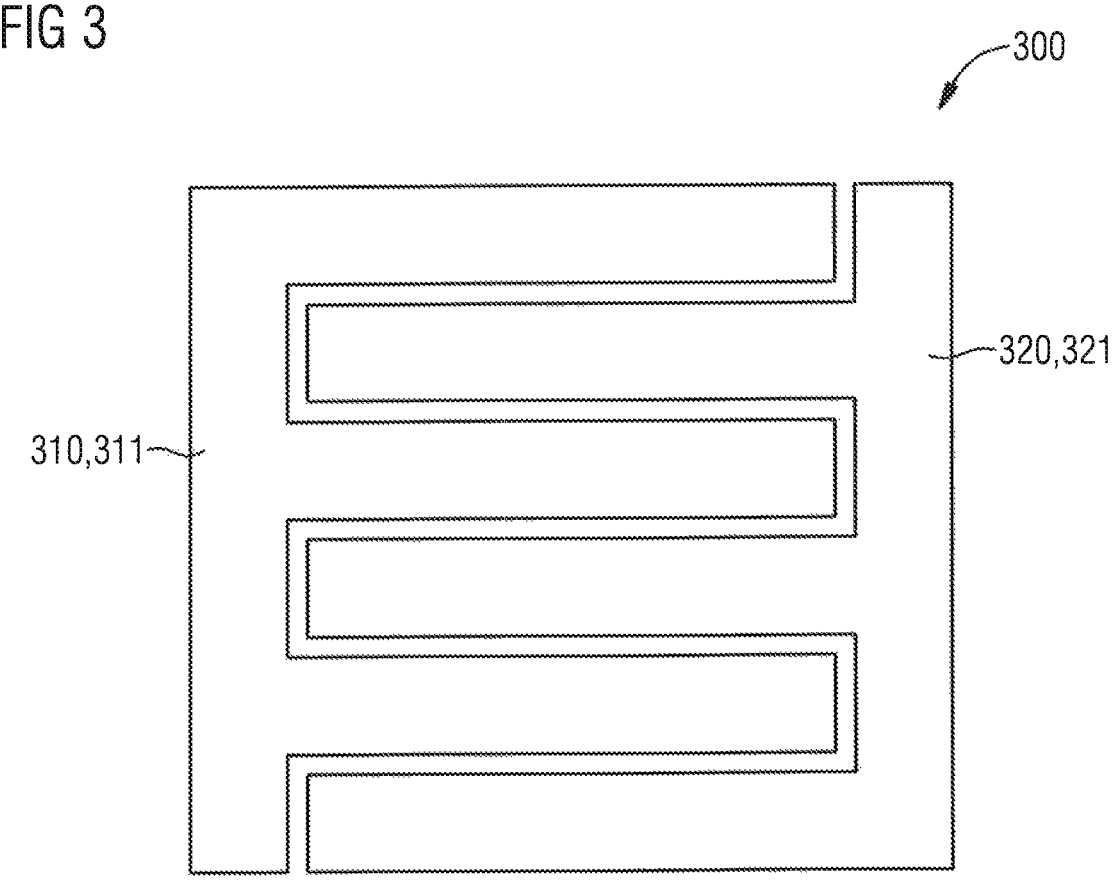
FIG. 3 schematically shows a plan view of the light detection device according to one example.

FIG. 3 shows in a schematized representation a plan view of the first light reception surface 311 of the first light detector 310 and of the second light reception surface 321 of the second light detector 320 of the light detection device 300 of the pulse oximetry device 100. The light reception surface 311 of the first light detector 310 and the second light reception surface 321 of the second light detector 320 are arranged in a common plane and are interleaved with one another. In the example shown in FIG. 3, the first light reception surface 311 and the second light reception surface 321 each have a comb-shaped finger structure. The finger structures of the first light reception surface 311 and the finger structure of the second light reception surface 321 are interdigitated with one another. By the interleaved arrangement of the first light reception surface 311 and the second light reception surface 321, it is possible to ensure that the first light reception surface 311 and the second light reception surface 321 are essentially illuminated equally by the light 211, 221 reflected or transmitted in the body part 500, without geometrical effects, for example, shadowing, leading to different brightnesses recorded by the first light detector 310 and by the second light detector 320. It is, however, also possible to configure the light reception surfaces 311, 321 of the light detectors 310, 320 of the light detection device 300 other than as represented in FIG. 3.

Figure 4:
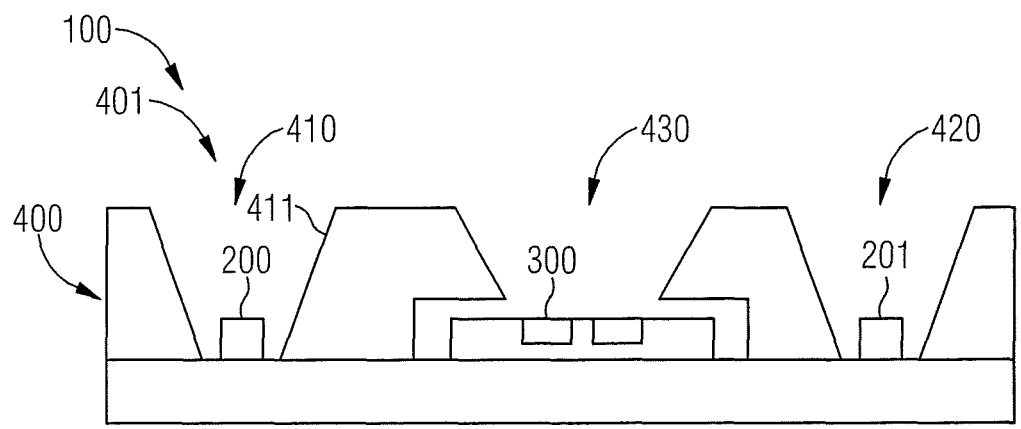
FIG. 4 schematically shows a sectional side view of a housing of the pulse oximetry device according to a first example.

FIG. 4 shows a schematic sectional side view of an exemplary housing 400 of the pulse oximetry device 100.

The housing 400 may, for example, be manufactured in chip-on-board or MID technology.

The housing 400 has an emitter cavity 410, a further emitter cavity 420 and a detector cavity 430. The three cavities 410, 420, 430 are arranged next to one another and are all open toward an upper side 401 of the housing 400. The cavities 410, 420, 430 are therefore configured as recesses arranged on the upper side 401 of the housing 400. The emitter cavities 410, 420 of the housing 400 widen from the respective bottom region of the cavities 410, 420 toward the upper side 401 of the housing 400 in the shape of a funnel. The detector cavity 430 may also widen from its bottom region toward the upper side 401 of the housing 400.

The light emission device 200 of the pulse oximetry device 100 is arranged at the bottom region of the emitter cavity 410 of the housing 400. Light 211, 221 emitted by the light emission device 200 can emerge from the emitter cavity 410 on the upper side 401 of the housing 400. A wall 411 of the emitter cavity 410 widening conically toward the upper side 401 may form an optical reflector, which may cause concentration of the light 211, 221 emitted by the light emission device 200.

Arranged in the further emitter cavity 420 of the housing 400, there is a further light emission device 201 configured in the same way as the light emission device 200 arranged in the emitter cavity 410. The further light emission device 201 arranged in the further emitter cavity 420 may be used to illuminate a larger skin surface of the body part 500 of the patient to be examined with the pulse oximetry device 100. The further emitter cavity 420 and the further light emission device 201 arranged in the further emitter cavity 420 may, however, also be omitted.

The first light detector 310 and the second light detector 320 of the light detection device 300 are arranged at the bottom region of the detector cavity 430 of the housing 400 of the pulse oximetry device 100. As an alternative, it would be possible to arrange the first light detector 310 and the second light detector 320 of the light detection device 300 in separate cavities. It is, however, preferred to arrange both light detectors 310, 320 of the light detection device 300 in the common detector cavity 430. A wall of the detector cavity 430 widening toward the upper side 401 of the housing 400 may be used to collect light incident in the detector cavity 430 and to direct it to the light reception surfaces 311, 321 of the light detectors 310, 320 of the light detection device 300.

Since the light emission device 200 and the light detection device 300 of the pulse oximetry device 100 are arranged in separate cavities 410, 420, 430 of the housing 400 of the pulse oximetry device 100, direct crosstalk between the light emission device 200 and the light detection device 300 is advantageously reduced or entirely avoided. This means that none, or only a little, of the light 211, 221 emitted by the light emission device 200 reaches the light detection device 300 on a direct path, but only does so after reflection in the body part 500 to be examined.

An optically transparent casting material, for example, a casting material which comprises silicone, may be arranged in the cavities 410, 420, 430 of the housing 400. In this case, the light emission device 200, the further light emission device 201 and/or the light detection device 300 are embedded in the casting material arranged in the respective cavity 410, 420, 430, and are thereby protected from damage by external influences. A casting material may also be arranged only in the emitter cavities 410, 420 or only in the detector cavity 430.

Figure 5:
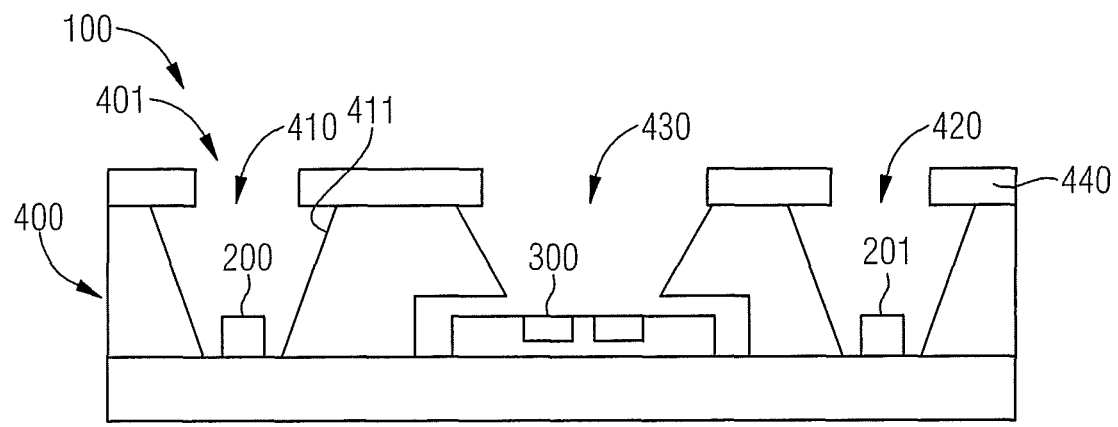
FIG. 5 schematically shows a sectional side view of the housing of the pulse oximetry device according to a second example.

FIG. 5 shows a schematic sectional side view of the housing 400 of the pulse oximetry device 100 according to an alternative example. The variant of the housing 400 as shown in FIG. 5 differs from the variant of the housing 400 as represented in FIG. 4 in that a diaphragm structure 440 is arranged on the upper side 401 of the housing 400. The diaphragm structure 440 may be configured in one piece continuously with the part of the housing 400 comprising cavities 410, 420, 430, or it may be arranged as a separate component on the upper side 401 of the housing 400. In its regions arranged over the cavities 410, 420, 430, the diaphragm structure 440 has diaphragm openings. The diaphragm openings may have diameters which are less than the aperture diameters of the cavities 410, 420, 430. In this way, the diaphragm structure 440 may cause a further reduction of undesired crosstalk between the light emission devices 200 and the light detection device 300 of the pulse oximetry device 100.

Figure 6:
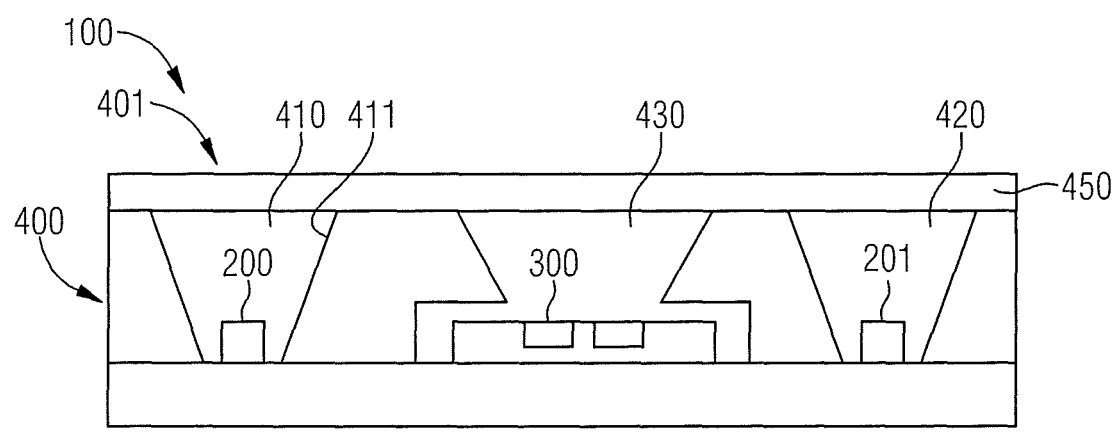
FIG. 6 schematically shows a sectional side view of the housing of the pulse oximetry device according to a third example.

FIG. 6 shows a schematic sectional side view of another alternative example of the housing 400 of the pulse oximetry device 100. The example of the housing 400 as shown in FIG. 6 differs from the example of the housing 400 as shown in FIG. 4 by a cover structure 450 arranged on the upper side 401 of the housing 400 and fully covering the upper side 401 of the housing 400, including the openings of the cavities 410, 420, 430. The cover structure 450 comprises an optically transparent material, for example, an optically transparent film. The cover structure 450 may, for example, be formed by a KAPTON film. The cover structure 450 may be used to protect the light emission devices 200 and the light detection device 300 of the pulse oximetry device 100 from damage by external influences. Furthermore, the cover structure 450 may cause a further reduction of undesired crosstalk between the light emission devices 200 and the light detection device 300.

Our devices and methods have been illustrated and described in detail with the aid of the preferred examples. This disclosure is not, however, restricted to the examples disclosed. Rather, other variants may be derived therefrom by those skilled in the art without departing from the protective scope of the appended claims.

This application claims priority of DE 10 2014 117 879.3, the subject matter of which is incorporated herein by reference.

The invention claimed is:

1. A pulse oximetry device comprising:
    a light emission device configured to emit light with a wavelength in a first wavelength interval and light with a wavelength in a second wavelength interval,
    a first light detector configured to detect light with the wavelength in the first wavelength interval, but not to respond to light with the wavelength in the second wavelength interval, and
    a second light detector configured to detect the light with the wavelength in the first wavelength interval and detect the light with the wavelength in the second wavelength interval,
    wherein the first light detector has a first light reception surface, the second light detector has a second light reception surface, and
    the first light reception surface and the second light reception surface are arranged in a common plane and are interleaved with one another.

2. The pulse oximetry device according to claim 1, wherein the first wavelength interval and the second wavelength interval do not overlap one another.

3. The pulse oximetry device according to claim 2, wherein the first wavelength interval or the second wavelength interval lies below a wavelength of 810 nm, and the other wavelength interval lies above a wavelength of 810 nm.

4. The pulse oximetry device according to claim 1, wherein the first light detector has a filter configured to filter out the light with the wavelength in the second wavelength interval.

5. The pulse oximetry device according to claim 1, wherein the light emission device is configured to emit the light with the wavelength in the second wavelength interval with a higher power than the light with the wavelength in the first wavelength interval.

6. The pulse oximetry device according to claim 1, wherein the light emission device has a first light-emitting diode structure configured to emit the light with the wavelength in the first wavelength interval, and a second light-emitting diode structure configured to emit the light with the wavelength in the second wavelength interval.

7. The pulse oximetry device according to claim 6, wherein the first light-emitting diode structure and the second light-emitting diode structure are arranged in a common light-emitting diode chip.

8. The pulse oximetry device according to claim 7, wherein the first light-emitting diode structure and the second light-emitting diode structure are arranged or stacked on top of one another.

9. The pulse oximetry device according to claim 6, wherein the light emission device has a first light-emitting diode chip having the first light-emitting diode structure, and a second light-emitting diode chip having the second light-emitting diode structure.

10. The pulse oximetry device according to claim 1, wherein the pulse oximetry device has a housing with an emitter cavity and a detector cavity,
the light emission device is arranged in the emitter cavity, and the first light detector is arranged in the detector cavity.

11. The pulse oximetry device according to claim 10, wherein the second light detector is arranged in the detector cavity.

12. The pulse oximetry device according to claim 10, wherein the emitter cavity and the detector cavity are open to a common surface of the housing.

13. The pulse oximetry device according to claim 10, wherein a wall of the emitter cavity forms an optical reflector.

14. The pulse oximetry device according to claim 10, wherein the housing has a further emitter cavity in which a further light emission device is arranged.

15. A method of operating a pulse oximetry device comprising:
    emitting light with a wavelength in a first wavelength interval and simultaneously emitting light with a wavelength in a second wavelength interval;
    recording a first measurement signal with a first light detector configured to detect the light with the wavelength in the first wavelength interval, but not to respond to the light with the wavelength in the second wavelength interval;
    recording a second measurement signal with a second light detector configured to detect the light with the wavelength in the first wavelength interval and detect the light with the wavelength in the second wavelength interval,
    wherein the first light detector has a first light reception surface, the second light detector has a second light reception surface, and
    the first light reception surface and the second light reception surface are arranged in a common plane and are interleaved with one another; and
    calculating an oxygen saturation from the first measurement signal and the second measurement signal.

16. The method according to claim 15, wherein a difference signal is formed by subtracting the first measurement signal from the second measurement signal, and
    the oxygen saturation is calculated from the first measurement signal and the difference signal.

17. The method according to claim 15, wherein the light with the wavelength in the second wavelength interval is emitted with a higher power than the light with the wavelength in the first wavelength interval.

* * * * *